US011567097B2

(12) United States Patent
Daume et al.

(10) Patent No.: US 11,567,097 B2
(45) Date of Patent: Jan. 31, 2023

(54) APPARATUS FOR OPTICALLY MONITORING A DOSING OF A LIQUID TO BE PIPETTED

(71) Applicant: Siemens Healthcare Diagnostics Products GmbH, Marburg (DE)

(72) Inventors: Dominik Andreas Daume, Heidelberg (DE); Thorsten Michels, Gross-Gerau (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 264 days.

(21) Appl. No.: 16/899,560

(22) Filed: Jun. 11, 2020

(65) Prior Publication Data

US 2020/0393480 A1 Dec. 17, 2020

(30) Foreign Application Priority Data

Jun. 13, 2019 (EP) .................................... 19179863

(51) Int. Cl.

| | |
|---|---|
| ***G06K 9/00*** | (2022.01) |
| ***G01N 35/10*** | (2006.01) |
| ***G06T 7/62*** | (2017.01) |
| ***G01F 22/00*** | (2006.01) |
| ***G01N 33/487*** | (2006.01) |
| ***G01N 35/00*** | (2006.01) |
| ***G06T 7/00*** | (2017.01) |
| ***H04N 5/225*** | (2006.01) |

(52) U.S. Cl.

CPC ......... *G01N 35/1009* (2013.01); *G01F 22/00* (2013.01); *G01N 33/487* (2013.01); *G01N 35/0099* (2013.01); *G06T 7/0012* (2013.01); *G06T 7/62* (2017.01); *H04N 5/2256* (2013.01); *G01N 2035/00178* (2013.01); *G01N 2035/1025* (2013.01); *G06T 2207/20081* (2013.01)

(58) Field of Classification Search

CPC ................................................ G01N 2035/103

See application file for complete search history.

(56) References Cited

U.S. PATENT DOCUMENTS

| | | | | |
|---|---|---|---|---|
| 5,601,980 A | 2/1997 | Gordon et al. | | |
| 2003/0049861 A1* | 3/2003 | Woodward | B01L 3/0262 | 422/922 |
| 2004/0019462 A1* | 1/2004 | Gehrlein | B01F 29/62 | 702/188 |
| 2012/0309636 A1* | 12/2012 | Gibbons | C12Q 1/48 | 435/6.12 |
| 2013/0252848 A1* | 9/2013 | Okano | A01N 1/0284 | 506/10 |
| 2015/0308944 A1* | 10/2015 | Bjornson | G01N 21/17 | 250/564 |
| 2017/0326549 A1* | 11/2017 | Jones | G01N 33/487 | |
| 2018/0348247 A1* | 12/2018 | Ando | G01N 35/1011 | |
| 2019/0151840 A1 | 5/2019 | Berberich et al. | | |

* cited by examiner

*Primary Examiner* — Hadi Akhavannik

(74) *Attorney, Agent, or Firm* — Dugan & Dugan, PC

(57) ABSTRACT

The invention relates to an apparatus for optically monitoring the dosing of a liquid to be pipetted for an automatic analysis unit. The apparatus comprises a dosing device, comprising a pipetting needle for pipetting the liquid, a lighting device for illuminating a drop of the liquid adhering to the pipetting needle, a camera with a set of optics to capture an image of the drop of the liquid, and an evaluation device for characterizing the drop of liquid by means of an automatic analysis of the image of the drop of liquid.

20 Claims, 2 Drawing Sheets

1 2 4 10 7 5 8 10 6 3

1
2
10
4
7
5
8
10
3
6

1
10
3
2
4
9
5
6

APPARATUS FOR OPTICALLY MONITORING A DOSING OF A LIQUID TO BE PIPETTED

CROSS REFERENCE TO RELATED APPLICATIONS

This claims priority to European Patent Application No. EP 19179863.6, filed Jun. 13, 2019, which is hereby incorporated. by reference herein in its entirety for all purposes.

FIELD

The invention relates to an apparatus for optically monitoring the dosage of a liquid to be pipetted for an automatic analysis unit.

BACKGROUND

Numerous testing and analysis methods for determination of physiological parameters in bodily fluid samples or other biological samples are now carried out automatically in large numbers in automated analysis units, also known as in-vitro diagnostic systems.

Modern analysis units are able to perform a wide range of detection reactions and analyses with one sample. In order to carry out a plurality of examinations automatically, various devices are required for spatially transferring measurement cells, reaction containers and reagent containers, such as transfer arms with gripper function, conveyor belts or rotating transport wheels, as well as devices for transferring liquids, such as pipetting devices. The devices comprise a control unit, which using appropriate software is able to plan and process the work steps for the desired analyses largely automatically.

Many of the analytical techniques used in such automated analysis units are based on optical methods. These methods enable the qualitative and quantitative testing of analytes, i.e., the substances to be detected or determined in samples. The determination of clinically relevant parameters, such as the concentration or activity of an analyte, is often carried out by mixing a part of a sample with one or more test reagents in a reaction vessel, which may also be the measurement cell, a process which, for example, initiates a biochemical reaction or a specific binding reaction that causes a measurable change in an optical or other physical property of the assay.

For example, in automated analysis units used to examine biological bodily fluids, for example, the required reagents are placed in a measuring cuvette using a pipetting device with a pipetting needle. The measuring cuvette is automatically moved into different positions with a cuvette gripper inside the automatic analysis unit using a robot arm, which is part of a robot station. After the measurement, the measuring cuvette used is transported through a waste chute into a waste container for disposal.

In automatic analysis units, the process often involves liquids being transported in very small quantities. This is carried out, for example, by motorized displaceable pipettes, wherein the pipettes are operated by motor-driven pumps. The pump generates a defined overpressure during the delivery of the liquid and a defined negative pressure during the collection of the fluid. The pipette is filled with an incompressible system fluid to ensure that the pressure conditions or pressure changes specified by the pump are recreated at the tip of the pipette with minimum loss, thus ensuring a high level of pipetting precision.

In medical devices such as diagnostic analyzers for automatic analysis of in-vitro samples, errors in the dosing of liquids and drop dispensing by means of the pipettes can lead to inaccuracies in the measurements and incorrect measurement results. Such errors in the drop dispensing are caused, for example, by incorrect dosing at the dosing units.

Monitoring and subsequent verification in automatic analyzers has usually been carried out up to now by using capacitive measurements to determine the pipetted fluid quantity during the dispensing of the liquid to be dosed by the pipettor, or when immersing the pipette needle in the liquid being pipetted, in order to detect any deviations in the fill level due to, e.g., a malfunction of the dosing unit. Alternatively, pressure measurements would be performed during the dispensing of the liquid to be dosed by the pipette.

When dispensing, e.g., reagents onto an inclined wall in a vessel through a pipettor for optimal dispensing of very small amounts of liquid, it may sometimes occur that there is no controlled fluid separation and some or all of the fluid will stick to the pipette needle and not be dispensed properly. Even a capacitive measurement or pressure measurement is also difficult to achieve in this case, since due to the lack of an earth there is no counter electrode. The liquid runs down the inclined wall and is therefore no longer in contact with the pipette. For single dosing operations, it has therefore previously not been possible to subsequently check the changed filling level and hence to verify the correct function of the dosing unit.

The apparatuses from the prior art therefore do not always allow a reliable monitoring of the dosing of pipetted liquids in automatic analysis units.

SUMMARY OF THE INVENTION

An object of the invention is therefore to provide an improved apparatus and an improved method for monitoring the dosing of a pipetted fluid for an automatic analysis unit.

This object is achieved according to the invention by the objects and methods described in the following.

It has been found that an improved apparatus for monitoring the dosage of a liquid to be pipetted for an automated analysis unit can be achieved by visually monitoring the dosing process using a camera and evaluating images of a drop of the liquid that adheres to the pipetting needle and then characterizing the drop accordingly. The dosing itself is usually monitored by means of an appropriately automated running monitor of the drive motor of the piston of an associated pumping system. However, this cannot be used to indicate, for example, whether the entire volume of the liquid to be pipetted has actually been dispensed, e.g., into a reaction vessel, and whether the dosing has been carried out correctly, or whether a significant residual amount of the liquid. remains stuck, e.g., to the tip of the pipetting needle. Optical monitoring has the advantage that the dosing process can be monitored with high precision. The monitoring is contactless and independent of the dosing process, so that interfering variables and inaccuracies which arise, for example, due to lamella separation when the pipetting needle emerges from the liquid in capacitive level measurement, are avoided. In dosing processes in which a single quantity of liquid is dispensed and where capacitive measurement is not possible, for example because the surrounding medium is not liquid, the apparatus according to the invention enables for the first time a precise monitoring of the actual dosing process performed. Similar advantages are obtained for the monitoring of dosing processes in which liquid is dispensed onto an inclined wall and so drops of liquid can slide down the wall.

The subject matter of the present invention is in particular an apparatus for optically monitoring the dosing of a liquid to be pipetted for an automatic analysis unit, the apparatus comprising:

a dosing device, comprising a pipetting needle for pipetting the liquid, a lighting device for illuminating a drop of the liquid adhering to the pipetting needle, a camera with a set of optics to capture an image of the drop of liquid, and an evaluation device for characterizing the drop of liquid by means of an automatic analysis of the image of the drop of liquid.

Preferably, the evaluation device comprises one or more field programmable gate arrays (FPGAs) and/or a computer, wherein the computer preferably comprises one or more graphics cards for image processing.

The camera is preferably connected to a computer and/or an FPGA and/or a microcontroller or other suitable data processing machine.

Preferably, the apparatus according to the invention comprises a trigger device that can transmit a trigger signal to the camera to capture an image of the drop of liquid and/or to the evaluation device for characterizing the drop of liquid. Preferably, a continuous or quasi-continuous image recording or evaluation can be started by the trigger signal.

Preferably, the trigger device comprises a light barrier, e.g., a fork-type light barrier and/or a distance sensor, wherein the distance sensor determines a distance preferably by means of a time of flight measurement and/or triangulation. Preferably, the distance sensor can also be an ultrasonic distance sensor, an inductive distance sensor, and/or a distance sensor based on a variable luminous flux.

The trigger signal can preferably be initiated by means of the trigger device in response to a movement of a piece of apparatus. The apparatus can be, for example, a cuvette and/or the pipetting needle. The apparatus is preferably part of an automatic analysis unit.

In another preferred embodiment, the trigger signal can also be generated, for example, via a device which in turn controls the movement of another device.

The trigger device preferably comprises, e.g., an electronic and/or optical component for triggering an operation, preferably a switching operation.

In a preferred design, the lighting device comprises a ring illuminator.

In another preferred design, the ring illuminator is arranged on the camera and/or optics.

In another preferred design, the lighting device comprises a mirror. Preferably, the mirror is arranged such that the drop of liquid can be imaged via the mirror using the optics of the camera.

In another preferred design, the lighting device comprises a beam splitter. Preferably, the beam splitter is arranged such that the drop of liquid can be imaged via the beam splitter using the optics of the camera. The illumination of the drop of the liquid is advantageously coupled in by the lighting device using the beam splitter.

In another preferred design, the lighting device comprises at least one light source, preferably more than one light source, particularly preferably three light sources.

A further subject of the invention is a method for optically monitoring the dosing of a liquid to be pipetted for an automatic analysis unit by acquiring an image of a drop of the liquid, preferably using an apparatus according to the invention for optically monitoring the dosing of a liquid to be pipetted, the method comprising the following steps:

dosing the liquid by pipetting using the dosing device, using a lighting device to illuminate a drop of the liquid adhering to the pipette needle after the dosing is completed, acquiring the image of the drop of the liquid using the optics and the camera, characterizing the drop by means of the evaluation device and the automatic analysis of the images of the drop of liquid.

Preferably, the acquisition of the image of the drop is initiated by a trigger signal from a trigger device, which is transmitted to the camera by the trigger device. Alternatively, the acquisition can also be performed continuously, independently of a trigger signal.

Preferably, the characterization of the drop by means of the evaluation device is initiated by a trigger signal, from a trigger device, which is transmitted to the evaluation device by the trigger device. Alternatively, the characterization of the drop can also be performed continuously, independently of a trigger signal.

Preferably, a continuous or quasi-continuous image recording or evaluation can be started by the trigger signal. The image recording and/or evaluation is preferably carried out until a further trigger signal triggers a corresponding termination, or until a predefined period of time has elapsed.

The trigger signal is preferably initiated by means of the trigger device in response to a movement of a piece of apparatus. The apparatus can be, for example, a cuvette and/or the pipetting needle. The apparatus is preferably part of an automatic analysis unit.

In another preferred embodiment, the trigger signal is generated via a device which in turn controls a movement of another device.

In a preferred implementation of the method, the characterization of the drop of liquid comprises the determination of the outline of the drop.

In a further preferred implementation of the method, the characterization of the drop of liquid comprises the determination of the volume of the drop.

In a further preferred implementation of the method, the determination of the volume of the drop of liquid comprises at least one assumption concerning the symmetry of the drop. The drop is preferably assumed to be symmetrical about at least one rotation axis.

In a further preferred implementation of the method, the characterization of the drop of liquid comprises a contactless detection of the quantity of liquid in the drop. Preferably, the detected quantity of liquid in the drop is also used to determine whether the dosing of the liquid has been performed correctly, and/or a quality of the dosing is determined, which is preferably carried out by means of the evaluation device. For example, if the volume of liquid detected exceeds a predefined absolute limit or a predefined variable limit, which depends, e.g., on the quantity of liquid to be pipetted, then the liquid dosing has not proceeded correctly; otherwise it has proceeded correctly. If the dosing has not taken place in the proper manner, an appropriate characterization of the dosing process is advantageously performed automatically and communicated to the laboratory personnel via a corresponding display on a monitor or on a paper printout, for example. Alternatively, a corresponding measurement process can also be automatically aborted and restarted, for example.

Alternatively, the detected quantity of liquid of the drop is advantageously used as a correction value and the actual dosing that was carried out is determined by deducting the detected quantity of liquid in the drop from a planned dosage. Optionally, an appropriate additional dosing can then advantageously be carried out, which adds the missing amount of liquid. This has the advantage that incorrect measurements are avoided and/or can be identified as such.

In a preferred implementation of the method, the determination of whether the liquid dosing has proceeded correctly and/or of the quality of the dosing is made by means of machine learning and/or comprises the use of a machine learning system.

In a preferred embodiment, the volume of the drop adhering to the pipetting needle is determined firstly by weighing out the corresponding quantity of liquid and then comparing it using image data for a plurality of drops. The image data comprise the images of the drops. A calibration is therefore preferably carried out in advance. This is preferably followed by assigning an appropriate quality to the dosing of the liquid using machine learning.

Preferably, a method according to the invention is carried out partially or completely by means of an apparatus according to the invention. This preferably involves capturing the image of the drop of liquid using an apparatus according to the invention.

Another subject of the invention is an analysis unit which comprises an aforementioned apparatus according to the invention for optically monitoring the dosing of a liquid to be pipetted and/or which is configured such that it can carry out a method according to the invention. The analysis unit also advantageously comprises an automatic cuvette gripper and/or an automatic pipettor.

A further subject of the invention is the use of an apparatus according to the invention for optically monitoring a dosing of a liquid to be pipetted in an automatic analysis unit, wherein the automatic analysis unit preferably comprises an automatic cuvette gripper and/or an automatic pipettor.

For the purposes of the invention, a "sample" means the material that is presumed to contain the substance (the analyte) to be detected. In particular, the term "sample" covers biological fluids of humans or animals such as blood, plasma, serum, sputum, exudate, bronchoalveolar lavage, lymphatic fluid, synovial fluid, seminal fluid, vaginal mucus, feces, urine, CSF, but also appropriately prepared tissue or cell culture samples, e.g., by homogenization or cell lysis for the photometric, preferably nephelometric analysis. In addition, for example, liquids or tissues of vegetable origin, forensic samples, water and sewage samples, foodstuffs, medicinal products may also act as samples, which may need to be suitably pre-treated before the analysis.

A quantitative test measures the amount, concentration or activity of the analyte in the sample. The term "quantitative test(ing)" also includes semi-quantitative methods that can only measure the approximate amount, concentration or activity of the analyte in the sample, or can only be used to indicate relative quantities, concentrations or activity. A qualitative test is the detection of the presence or absence of the analyte in the sample, or the indication that the amount, concentration or activity of the analyte in the sample is above or below one or more specific threshold values.

For example, a measuring cuvette is a cuvette or a reaction vessel made of glass, plastic or metal. The measuring cuvette is advantageously manufactured from optically transparent materials, which can be particularly advantageous when using optical analysis methods.

The terms "measuring cuvette" and "cuvette" are used interchangeably and refer to the same object.

The terms "analysis unit" and "analyzer" are used here interchangeably and refer to the same object.

A drop of a liquid is a quantity of the liquid that can be present, for example, in the form of a film of liquid, in shapes similar to the shape of bulbs, or as spherical droplets of liquid. The quantity of the liquid preferably involves quite small quantities of liquid, which can be, e.g., in the range of 1 to 100 microliters, preferably in the range of 5 to 10 microliters.

The camera preferably comprises a digital recording device comprising a charge-coupled device (CCD) chip or a plurality of CCD chips. The digital recording device is particularly preferably based on a Complementary Metal-Oxide-Semiconductor (CMOS) technology and/or comprises a CMOS chip. The camera may also preferably be a digital recording device.

BRIEF DESCRIPTION OF THE DRAWINGS

Examples of the invention will now be described in further detail by reference to drawings. In the figures.

Equivalent parts are labeled with the same reference signs in all figures.

DETAILED DESCRIPTION OF THE INVENTION

The apparatus (1) according to FIGS. 1 to 4 is embedded in an analysis unit, not shown in detail, which is designed to perform a wide range of analyses of samples. To this end, the automatic analysis unit comprises a plurality of pipetting devices and transport devices, not shown, in addition to a control unit for the automated evaluation of the analyses, and an evaluation device (6) for characterizing a drop (4) of a liquid adhering to the dosing device (2) by means of an automatic evaluation of an image of the drop (4) of liquid. Each apparatus (1) is designed for optically monitoring the dosing of a liquid to be pipetted for an automated analysis unit.

Figure 1:
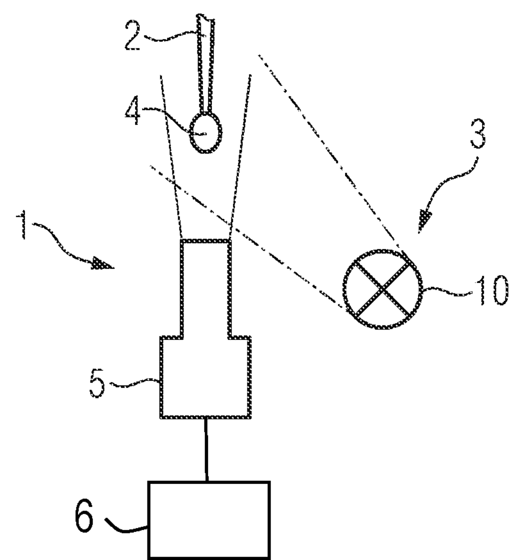
FIGS. 1, 2, 3, and 4 schematically show the structure of different advantageous embodiments of an apparatus for optically monitoring a dosing of a liquid to be pipetted for an automatic analysis unit.

In the embodiment of the apparatus (1) shown in FIG. 1, a drop (4) of a liquid is pipetted by means of the dosing device (2). The drop (4) adheres to the tip of a pipetting needle. Below the drop (4) a camera (5) with a set of optics is arranged. The drop is directly illuminated from below at an angle by means of a lighting device (3), wherein the lighting device (3) comprises a light source (10).

Figure 2:
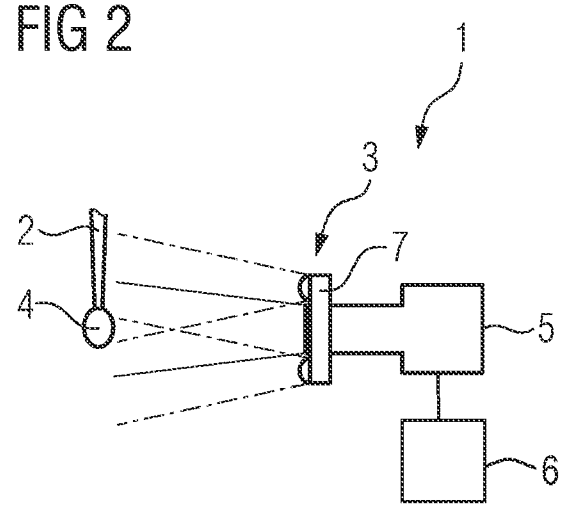

In the embodiment of the apparatus (1) shown in FIG. 2, a drop (4) of a liquid is pipetted by means of the dosing device (2). The drop (4) adheres to the tip of a pipetting needle. At the level of the drop (4), a camera (5) with an optical system is arranged to one side. The drop is illuminated from the side by means of a lighting device (3), which is designed as a ring illuminator (7). The ring illuminator (7) is arranged on the optics of the camera (5).

Figure 3:
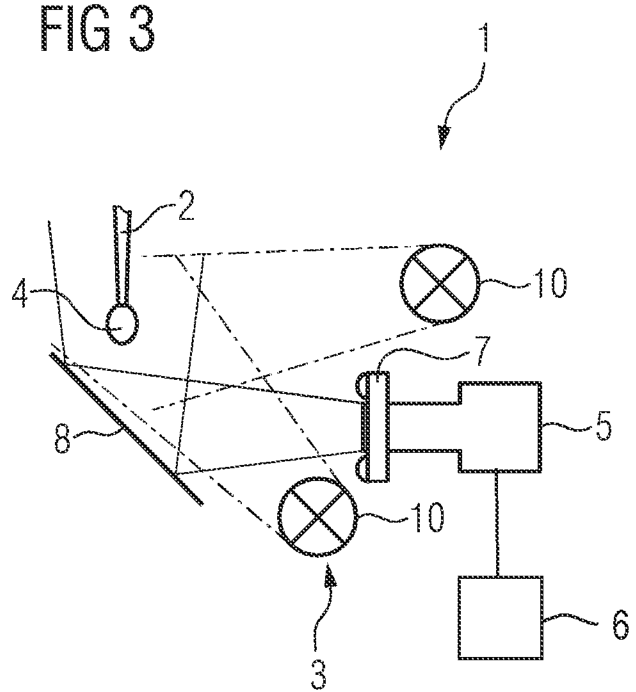

In the embodiment of the apparatus (1) shown in FIG. 3, a drop (4) of a liquid is pipetted by means of the dosing device (2). The drop (4) is located at the tip of a pipetting needle. Slightly below the level of the drop (4), a camera (5) with a set of optics is arranged to one side. The drop is illuminated from the side by means of a lighting device (3), which comprises a ring illuminator (7) arranged on the optical system of the camera (5), and two other light sources (10). Both the ring illuminator (7) and the two other light sources (10) directly illuminate the drop (10). Further, an optical mirror (8) is located below the drop (4) at an angle to the optical axis of the camera (5). The imaging of the drop by means of the optics of the camera (5) is carried out via the mirror (8).

Figure 4:
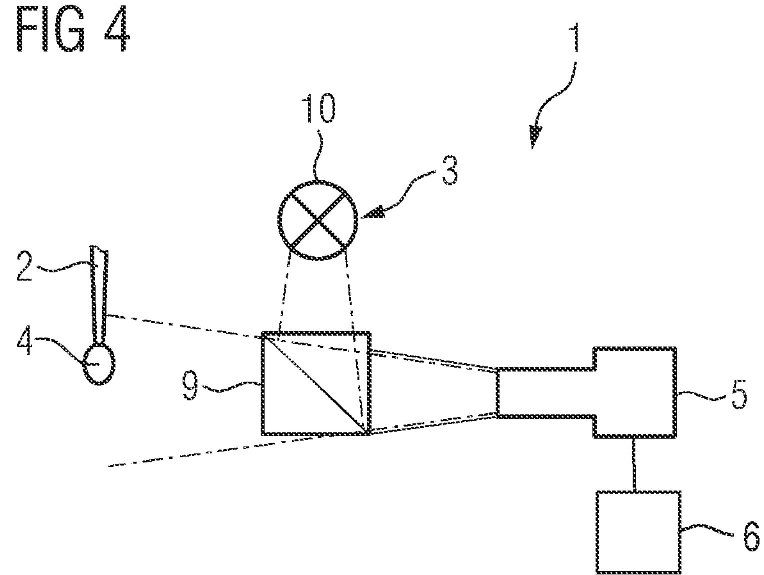

In the embodiment of the apparatus (1) shown an FIG. 4, a drop (4) of a liquid is pipetted by means of the dosing device (2). The drop (4) adheres to the tip of a pipetting needle. At the level of the drop (4), a camera (5) with an optical system is positioned to one side. A beam splitter (9) is arranged between drop (4) and camera (5). Above the beam splitter (9), a lighting device (3) is provided, which comprises a light source (10). The light emerging from the light source is deflected by means of the beam splitter (9) and strikes the drop (4) along the optical axis of the camera (5) and illuminates it. The drop (4) is imaged through the beam splitter (9) using the optics of the camera.

LIST OF REFERENCE SIGNS

1 apparatus
2 dosing device
3 lighting device
4 drop
5 camera
6 evaluation device
7 ring illuminator
8 mirror
9 beam splitter
10 light source

The invention claimed is:

1. An apparatus for optically monitoring a dosing of a liquid to be pipetted for an automatic analysis unit, the apparatus comprising a dosing device comprising a pipetting needle for pipetting the liquid, a lighting device for illuminating a drop of the liquid adhering to the pipetting needle, a camera with a set of optics for capturing an image of the drop of the liquid only adhering to the pipetting needle, the camera arranged to a side of the drop of the liquid and the pipetting needle, and an evaluation device for characterizing the drop of the liquid via an automatic analysis of the image of the drop of the liquid and for using a detected quantity of the drop as a correction value to determine an additional dosing in response to the detected quantity of the drop not equaling a planned dosage.

2. The apparatus as claimed in claim 1, wherein the lighting device comprises a ring illuminator.

3. The apparatus as claimed in claim 2, wherein the ring illuminator is located on the camera or the optics.

4. The apparatus as claimed in claim 1, wherein the lighting device comprises a mirror.

5. The apparatus as claimed in claim 1, wherein the lighting device comprises a beam splitter.

6. The apparatus as claimed in claim 1, wherein the lighting device comprises at least one light source.

7. A method for optically monitoring the dosing of a liquid to be pipetted for an automatic analysis unit by acquiring an image of a drop of the liquid, the method comprising the following steps:

dosing of the liquid by pipetting using a dosing device, using a lighting device to illuminate a drop of the liquid adhering to the pipette needle after the dosing is completed, acquiring the image of the drop of the liquid only adhering to the pipetting needle from a side of the drop of the liquid and the pipetting needle using a set of optics and a camera, characterizing the drop via an evaluation device and an automatic analysis of the image of the drop of the liquid, and an additional dosing of the liquid by pipetting using the dosing device to add an amount of the liquid in response to the characterizing determining that a detected quantity of the liquid in the drop is less than a planned dosage.

8. The method as claimed in claim 7, wherein the characterization of the drop of the liquid comprises the determination of the outline of the drop.

9. The method as claimed in claim 7, wherein the characterization of the drop of the liquid comprises the determination of the volume of the drop.

10. The method as claimed in claim 9, wherein the determination of the volume of the drop of the liquid comprises at least one assumption about the symmetry of the drop.

11. The method as claimed in claim 7, wherein via the characterization of the drop of the liquid, the quantity of liquid in the drop is detected in a contactless manner.

12. The method as claimed in claim 11, wherein the detected quantity of liquid in the drop is used to determine whether the dosing of the liquid has been performed correctly.

13. The method as claimed in claim 12, wherein the determination is carried out by machine learning or comprises the use of a machine learning system.

14. The method as claimed in claim 7, wherein the image of the drop of the liquid is acquired via an apparatus comprising:

the dosing device comprising a pipetting needle for pipetting the liquid, the lighting device, the camera with the set of optics, and the evaluation device, wherein the entire method is carried out via the apparatus.

15. An automatic analysis unit, wherein the automatic analysis unit comprises an apparatus as claimed in claim 1.

16. An automatic analysis unit, wherein the automatic analysis unit is configured to execute a method as claimed in claim 7, the automatic analysis unit having an automatic cuvette gripper or an automatic pipettor.

17. The apparatus as claimed in claim 1, wherein the lighting device comprises at least three light sources.

18. The method as claimed in claim 10, wherein the at least one assumption includes the drop being symmetric about at least one rotational axis.

19. The method as claimed in claim 11, wherein a quality of the dosing is determined.

20. The method as claimed in claim 19, wherein the quality of the dosing is determined via the evaluation device.

* * * * *